(12) United States Patent
Friedlander et al.

(10) Patent No.: US 9,182,314 B2
(45) Date of Patent: Nov. 10, 2015

(54) DETECTION OF PIPELINE CONTAMINANTS

(71) Applicant: INTERNATIONAL BUSINESS MACHINES CORPORATION, Armonk, NY (US)

(72) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 29 days.

(21) Appl. No.: 14/155,781

(22) Filed: Jan. 15, 2014

(65) Prior Publication Data

US 2014/0129155 A1    May 8, 2014

Related U.S. Application Data

(63) Continuation of application No. 13/190,172, filed on Jul. 25, 2011, now Pat. No. 8,788,222.

(51) Int. Cl.
*G01F 17/00* (2006.01)
*G01M 7/02* (2006.01)
(Continued)

(52) U.S. Cl.
CPC .............. *G01M 7/022* (2013.01); *G01N 9/002* (2013.01); *G01N 9/32* (2013.01); *G01N 29/14* (2013.01); *G01N 29/4436* (2013.01);
(Continued)

(58) Field of Classification Search
CPC ............ G01M 7/022; G01N 2291/021; G01N 2291/022; G01N 2291/2634; G01N 29/14; G01N 29/4436; G01N 29/46; G01N 9/32

USPC .......................................... 702/39, 35, 40, 56
See application file for complete search history.

(56) References Cited

U.S. PATENT DOCUMENTS 3,820,381 A    6/1974   Thurston
3,838,421 A    9/1974   Dasse-Hartaut et al.
(Continued)

FOREIGN PATENT DOCUMENTS

JP    52104960 A    9/1977
JP     4235380 A    8/1992
(Continued)

OTHER PUBLICATIONS

UK IPO, GB Patent Application No. 1401834.5—Examination Report Mailed Mar. 18, 2014.
(Continued)

*Primary Examiner* — Michael Nghiem
*Assistant Examiner* — Eman Alkafawi
(74) *Attorney, Agent, or Firm* — John R. Pivnichny; Law Office of Jim Boice (57) ABSTRACT

A computer-implemented method, system, and/or computer program product detects contaminants in a pipe that is transporting a known fluid. A baseline vibration pattern is established from readings generated by a smart sensor that is affixed to the pipe. This baseline vibration pattern is caused by a flow of the known fluid as the known fluid travels through the pipe in an unadulterated form. Subsequent readings from the smart sensor are taken to generate a new vibration pattern. In response to the new vibration pattern being different, beyond a predefined range, from the baseline vibration pattern, the new vibration pattern is matched to a known vibration pattern in order to identify a specific contaminant of the known fluid.

15 Claims, 6 Drawing Sheets

(51) Int. Cl.

| | | |
|---|---|---|
| G01N 9/00 | (2006.01) | |
| G01N 9/32 | (2006.01) | |
| G01N 29/14 | (2006.01) | |
| G01N 29/46 | (2006.01) | |
| G01N 29/44 | (2006.01) | |

(52) U.S. Cl.
CPC ......... *G01N 29/46* (2013.01); *G01N 2291/021* (2013.01); *G01N 2291/022* (2013.01); *G01N 2291/2634* (2013.01)

(56) References Cited

U.S. PATENT DOCUMENTS

| | | |
|---|---|---|
| 4,073,183 A | 2/1978 | Byalko et al. |
| 4,186,590 A | 2/1980 | Egorov et al. |
| 4,511,247 A | 4/1985 | McGovern et al. |
| 4,530,233 A | 7/1985 | Kadi |
| 4,715,743 A | 12/1987 | Schmanski |
| 5,195,046 A | 3/1993 | Gerardi et al. |
| 5,549,803 A | 8/1996 | Schoess et al. |
| 5,681,986 A | 10/1997 | Merk et al. |
| 5,736,940 A | 4/1998 | Burgener |
| 6,260,004 B1 | 7/2001 | Hays et al. |
| 6,265,979 B1 | 7/2001 | Chen et al. |
| 6,718,270 B2 | 4/2004 | Horiuchi et al. |
| 6,731,804 B1 * | 5/2004 | Carrieri et al. ............... 382/191 |
| 6,950,767 B2 | 9/2005 | Yamashita et al. |
| 7,228,740 B2 | 6/2007 | Sinha |
| 7,325,759 B2 | 2/2008 | Meyer |
| 7,343,136 B2 | 3/2008 | Liu et al. |
| 7,535,355 B2 | 5/2009 | Barone |
| 7,627,441 B2 | 12/2009 | Longsdorf et al. |
| 7,630,948 B2 | 12/2009 | Friedlander et al. |
| 7,693,663 B2 | 4/2010 | Friedlander et al. |
| 7,720,574 B1 | 5/2010 | Roys |
| 7,762,142 B2 | 7/2010 | Rakow et al. |
| 8,154,723 B2 | 4/2012 | Fu et al. |
| 8,538,667 B2 | 9/2013 | Friedlander et al. |
| 2002/0077749 A1 | 6/2002 | Doi |
| 2004/0122787 A1 | 6/2004 | Avinash et al. |
| 2005/0011278 A1 | 1/2005 | Brown et al. |
| 2005/0256885 A1 | 11/2005 | Yairi et al. |
| 2006/0071786 A1 | 4/2006 | Fano |
| 2006/0097983 A1 | 5/2006 | Haggman et al. |
| 2006/0285350 A1 | 12/2006 | Wang |
| 2007/0050121 A1 | 3/2007 | Ammon et al. |
| 2007/0199382 A1 | 8/2007 | Sakai |
| 2008/0009099 A1 | 1/2008 | Kishkovich et al. |
| 2008/0077463 A1 | 3/2008 | Friedlander et al. |
| 2008/0180281 A1 | 7/2008 | Bilimoria et al. |
| 2008/0270034 A1 | 10/2008 | Friedlander et al. |
| 2008/0274553 A1 | 11/2008 | Bratton et al. |
| 2009/0157302 A1 | 6/2009 | Tashev et al. |
| 2009/0271100 A1 | 10/2009 | Kim et al. |
| 2010/0125409 A1 | 5/2010 | Prehofer |
| 2010/0150359 A1 | 6/2010 | Knickrehm et al. |
| 2010/0189291 A1 | 7/2010 | Aharoni et al. |
| 2010/0268469 A1 | 10/2010 | Harrison et al. |
| 2011/0085156 A1 | 4/2011 | Jones et al. |
| 2011/0130956 A1 | 6/2011 | Tracton et al. |
| 2011/0153193 A1 | 6/2011 | Fox et al. |
| 2011/0153208 A1 | 6/2011 | Kruglick |
| 2011/0172907 A1 | 7/2011 | Rui Da Silva Freitas |
| 2011/0173067 A1 | 7/2011 | Herbst et al. |
| 2011/0238291 A1 | 9/2011 | Bach |
| 2011/0308638 A1 | 12/2011 | Hyland et al. |
| 2013/0030613 A1 | 1/2013 | Friedlander et al. |
| 2013/0030680 A1 | 1/2013 | Friedlander et al. |
| 2013/0030724 A1 | 1/2013 | Friedlander et al. |
| 2013/0030725 A1 | 1/2013 | Friedlander et al. |
| 2013/0040399 A1 | 2/2013 | Belbruno et al. |
| 2013/0085671 A1 | 4/2013 | Friedlander et al. |

FOREIGN PATENT DOCUMENTS

| | | |
|---|---|---|
| JP | 05052972 U | 7/1993 |
| JP | 07044117 A | 2/1995 |
| JP | 08085496 A | 4/1996 |
| JP | 2006194795 A | 7/2006 |
| JP | 2007531868 A | 11/2007 |
| WO | 2008052786 A1 | 5/2008 |
| WO | 2010071607 A1 | 6/2010 |

OTHER PUBLICATIONS

N. Harrington, "Knock-Based Commands for Your Linux Laptop", pp. 1-11, Jul. 25, 2006, http://www.ibm.com/developerworks/library/I-knockage/index.html.

W. Xie et al., "A New Diagnostic Method of Bolt Loosening Detection for Thermal Protection Systems", Proceedings of the SPIE—The International Society for Optical Engineering, vol. 7493, 2009.

S. Lihua et al., "Applications of Piezoelectric Material Sensors in Smart Structures", Transactions of Nanjing University of Aeronautics & Astronautics, vol. 1, No. 2, 210-213, Dec. 1996.

J. Schoess et al., "Smart Aircraft Fastener Evaluation (SAFE) System—A Condition-Based Corrosion Detection System for Aging Aircraft", Proceedings of the SPIE—The International Society for Optical Engineering, vol. 2718, 175-184, 1996.

J. Schoess et al., "Smart Fastener for KC-135 Structural Integrity Monitoring", Proceedings of the SPIE—The International Society for Optical Engineering, vol. 3042, pp. 278-282, 1997.

T. Bojko, "Smart Sensor Solutions for Mechanical Measurements and Diagnostics", Metrology and Measurement Systems, vol. 12, No. 1, 2005, pp. 95-103.

S. Kessler, "Piezoelectric-Based In-Situ Damage Detection of Composite Materials for Structural Health Monitoring Systems", Doctorate of Philosophy in Aeronautics and Astronautics at the Massachusetts Institute of Technology, 2002, pp. 1-200.

D. Sinha, "Acoustic Sensor for Pipeline Monitoring: Technology Report", Los Alamos National Laboratory, Jul. 20, 2005, pp. 1-23.

B. Umeadi et al., "The Development of an Intelligent Sensor for the Monitoring of Pipeline System Integrity", Oil and Gas 2008, pp. 1-4.

C. Zang et al., "Structural Health Monitoring and Damage Assessment Using Frequency Response Correlation Criteria", Journal of Engineering Mechanics, Sep. 2007, 981-993.

S.L. Hung et al., "Aiming for the Top University Plan: Preliminary Results" 2009, http://www.cv.nctu.edu.tw/~wwwadm/chinese/monitoring2/result.html.

U.S. Appl. No. 11/741,186, Friedlander et al.—Non-Final Office Action Mailed Nov. 21, 2008.

U.S. Appl. No. 11/741,186, Friedlander et al.—Final Office Action Mailed Apr. 15, 2009.

U.S. Appl. No. 11/741,186, Friedlander et al.—Non-Final Office Action Mailed Jul. 9, 2009.

U.S. Appl. No. 11/741,186, Friedlander et al.—Notice of Allowance Mailed Nov. 20, 2009.

R. Marinelli, "FAA Runway Friction Program", Runway Condition Determination, Reporting, and Report Dissemination Workshop, Jun. 20, 2006, pp. 1-13.

T. Yager, "Runway Friction Measurement", FAA/Aviation Industry Workshop on Runway Condition Determination, Reporting, and Report Dissemination, Aug. 7-8, 2006, pp. 1-15.

U.S. Appl. No. 13/192,887—Non-Final Office Action Mailed Feb. 7, 2013.

United Kingdom Patent Application No. GB1216790.4, Combined Search and Examination Report, Jan. 18, 2013, pp. 1-5.

International Searching Authority, International Search Report and Written Opinion for PCT/IB2012/053753, Dec. 18, 2012, pp. 1-6.

U.S. Appl. No. 13/252,342—Non-Final Office Action Mailed Nov. 9, 2012.

U.S. Appl. No. 13/962,665—Non-Final Office Action Mailed Sep. 27, 2013.

U.S. Appl. No. 13/192,149—Non-Final Office Action Mailed Sep. 27, 2013.

U.S. Appl. No. 13/190,172—Non-Final Office Action Mailed Sep. 25, 2013.

(56) References Cited

OTHER PUBLICATIONS

U.S. Appl. No. 13/962,665—Notice of Allowance Mailed Jan. 3, 2014.
U.S. Appl. No. 13/192,149—Final Office Action Mailed Feb. 26, 2014.
T. Robertson, GB Patent Application No. 1401834.5—Response to Examination Report mailed Jul. 8, 2014 (Remarks Only).
Douglas Equipment International Inc., Special Products Division, "Mu-Meter MK 6—Specification", PDF retrieved from http://www.douglas-equipment.com/product_display.php?id=0000000035, no publication date available, retrieval date: Nov. 3, 2011, pp. 1-2.

* cited by examiner

DETECTION OF PIPELINE CONTAMINANTS

BACKGROUND

The present disclosure relates to the field of electronics, and specifically to electronic devices used to measure vibration. Still more particularly, the present disclosure relates to sensors used to detect contaminants in a pipe.

SUMMARY

A computer-implemented method, system, and/or computer program product detects contaminants in a pipe that is transporting a known fluid. A baseline vibration pattern is established from readings generated by a smart sensor that is affixed to the pipe. This baseline vibration pattern is caused by a flow of the known fluid as the known fluid travels through the pipe in an unadulterated form. Subsequent readings from the smart sensor are taken to generate a new vibration pattern. In response to the new vibration pattern being different, beyond a predefined range, from the baseline vibration pattern, the new vibration pattern is matched to a known vibration pattern in order to identify a specific contaminant of the known fluid.

DETAILED DESCRIPTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
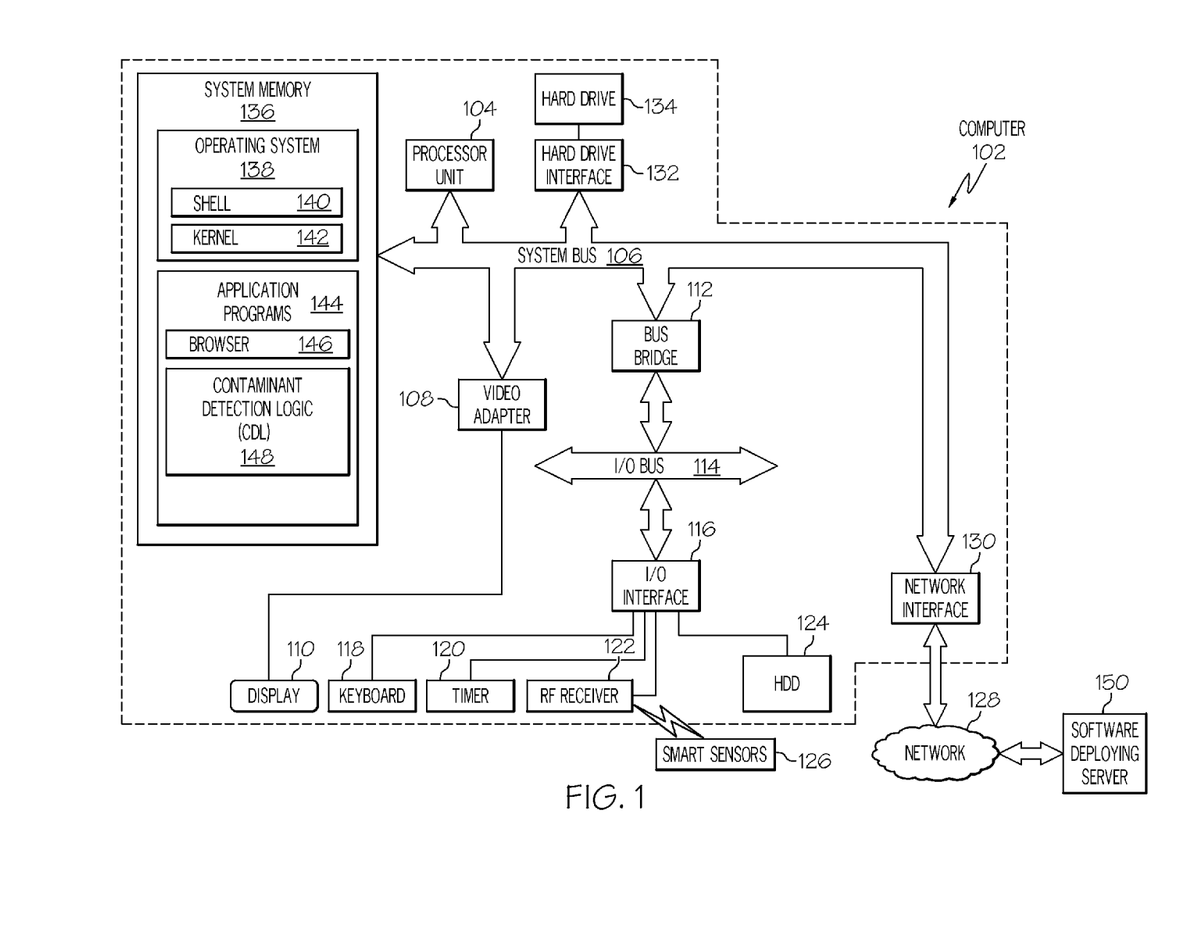
FIG. 1 depicts an exemplary computer which may be utilized by the present invention.

With reference now to the figures, and in particular to FIG. 1, there is depicted a block diagram of an exemplary computer 102, which the present invention may utilize. Note that some or all of the exemplary architecture shown for computer 102 may be utilized by software deploying server 150.

Computer 102 includes a processor unit 104, which may utilize one or more processors each having one or more processor cores, that is coupled to a system bus 106. A video adapter 108, which drives/supports a display 110, is also coupled to system bus 106. System bus 106 is coupled via a bus bridge 112 to an Input/Output (I/O) bus 114. An I/O interface 116 is coupled to I/O bus 114. I/O interface 116 affords communication with various I/O devices, including a keyboard 118, a timer 120, a Radio Frequency (RF) receiver 122, a Hard Disk Drive (HDD) 124, and smart sensors 126, which communicate wirelessly with the RF receiver 122. Note that, in one embodiment, elements 122 and 126 are hardwired together, such that readings from the sensors (e.g., element 126) are able to be transmitted via wiring to a receiver (e.g., element 122). Note also that the format of the ports connected to I/O interface 116 may be any known to those skilled in the art of computer architecture, including but not limited to Universal Serial Bus (USB) ports.

Computer 102 is able to communicate with a software deploying server 150 via a network 128 using a network interface 130, which is coupled to system bus 106. Network 128 may be an external network such as the Internet, or an internal network such as an Ethernet or a Virtual Private Network (VPN).

A hard drive interface 132 is also coupled to system bus 106. Hard drive interface 132 interfaces with a hard drive 134. In a preferred embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a World Wide Web (WWW) client (i.e., computer 102) to send and receive network messages to the Internet using HyperText Transfer Protocol (HTTP) messaging, thus enabling communication with software deploying server 150 and other described computer systems.

Application programs 144 in computer 102's system memory (as well as software deploying server 150's system memory) also include a Contaminant Detection Logic (CDL) 148. CDL 148 includes code for implementing the processes described below, and particularly as described in reference to FIGS. 2-9. In one embodiment, computer 102 is able to download CDL 148 from software deploying server 150, including in an on-demand basis. Note further that, in one embodiment of the present invention, software deploying server 150 performs all of the functions associated with the present invention (including execution of CDL 148), thus freeing computer 102 from having to use its own internal computing resources to execute CDL 148.

The hardware elements depicted in computer 102 are not intended to be exhaustive, but rather are representative to highlight essential components required by the present invention. For instance, computer 102 may include alternate memory storage devices such as magnetic cassettes, Digital Versatile Disks (DVDs), Bernoulli cartridges, and the like. These and other variations are intended to be within the spirit and scope of the present invention.

Figure 2:
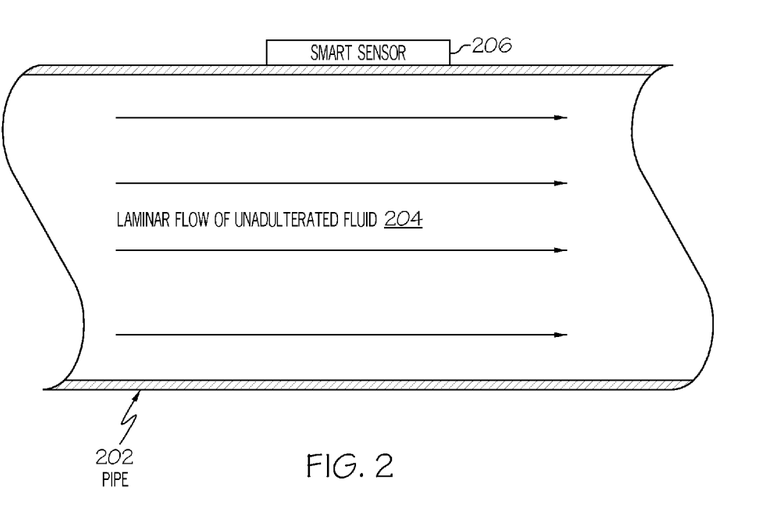
FIG. 2 illustrates an exemplary pipe through which unadulterated fluid is flowing.

With reference now to FIG. 2, an exemplary pipe 202, through which an unadulterated fluid 204 passes in one manner (e.g., as a smooth laminar flow), is presented. As the unadulterated fluid 204 has no foreign contaminants, and thus is homogeneous in its makeup, unadulterated fluid 204 is able to flow smoothly through the pipe 202. As the unadulterated fluid 204 moves in a known manner (e.g., smoothly) through the pipe 202, the smart sensor 206 is able to detect and generate a baseline vibration pattern, which is discussed in further detail below.

Figure 3:
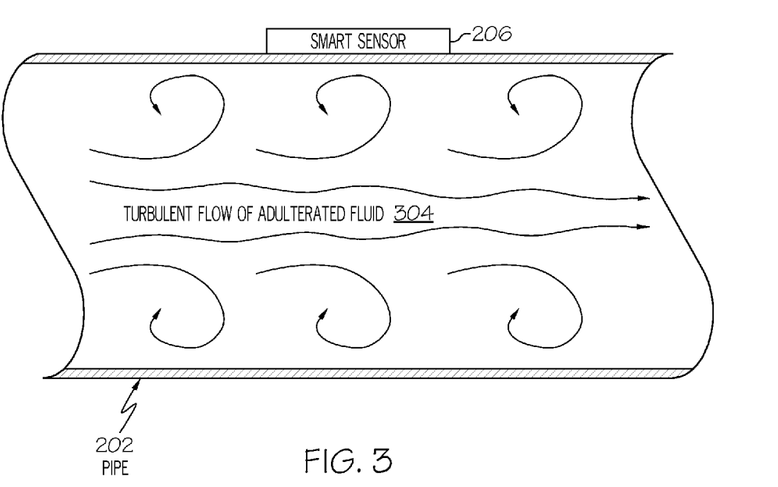
FIG. 3 depicts the pipe shown in FIG. 2 but with adulterated fluid flowing through the pipe.

However, if a contaminant were to be introduced to the unadulterated fluid 204 shown in FIG. 2, this would result in an adulterated fluid 304 passing through the pipe 202 in different manner, such as via an irregular turbulent flow. This turbulent flow causes a new vibration pattern to pass through the wall of the pipe 202. This new vibration pattern is detected and/or analyzed by the smart sensor 206, thus indicating the presence of the contaminant within the adulterated fluid 304.

Figure 4:
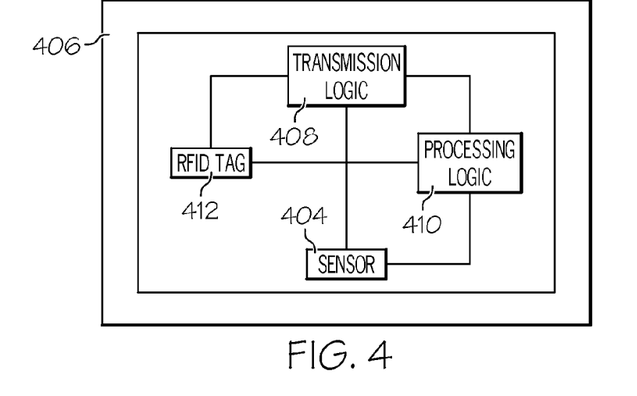
FIG. 4 illustrates an exemplary RFID enabled smart sensor that is affixed to the pipe shown in FIGS. 2-3.

Additional detail of an exemplary smart sensor, such as the smart sensor 206 depicted in FIGS. 2-3, is illustrated in FIG. 4 as an RFID-enabled smart sensor 406. Within the RFID-enabled smart sensor 406 is a sensor 404. Sensor 404 is able to sense mechanical vibration (i.e., vibrations that are propagated through a solid medium such as metal). In one embodiment, sensor 404 is also able to detect acoustic vibration (i.e., vibrations that are propagated through air) as well as radiation (i.e., levels of radioactivity) being emitted from fluids flowing through a pipe to which the smart sensor 206 is affixed.

In one embodiment, sensor 404 is directly coupled to a transmission logic 408, which is able to transmit the raw information detected by the sensor 404 to a receiver (e.g., RF receiver 122 shown in FIG. 1). For example, assume that sensor 404 detects mechanical vibrations through the use of an internal crystal-based strain gauge and/or accelerometer. The sensor 404 transduces these mechanical vibrations into electrical analog signals, which is directly transmitted by the transmission logic 408. In another embodiment, however, the transduced mechanical vibrations are first sent to a local processing logic 410 within the RFID-enabled smart sensor 406. This processing logic 410 is able to quantify and digitize the transduced mechanical vibrations before they are sent to the transmission logic 408.

Note that in one embodiment, an RFID tag 412 is also a component of the RFID-enabled smart sensor 406. The RFID tag 412, which is different/unique to each RFID-enabled smart sensor 406, identifies where on a pipe (e.g., pipe 202 shown above in FIGS. 2-3) a particular RFID-enabled smart sensor 406 is affixed. The RFID tags may be active (i.e., battery powered), semi-passive (i.e., powered by a battery and a capacitor that is charged by an RF interrogation signal), or purely passive (i.e., either have a capacitor that is charged by an RF interrogation signal or are geometrically shaped to reflect back specific portions of the RF interrogation signal). These passive RFID tags may contain an on-board Integrated Circuit (IC) chip, or they may be chipless.

Figure 5:
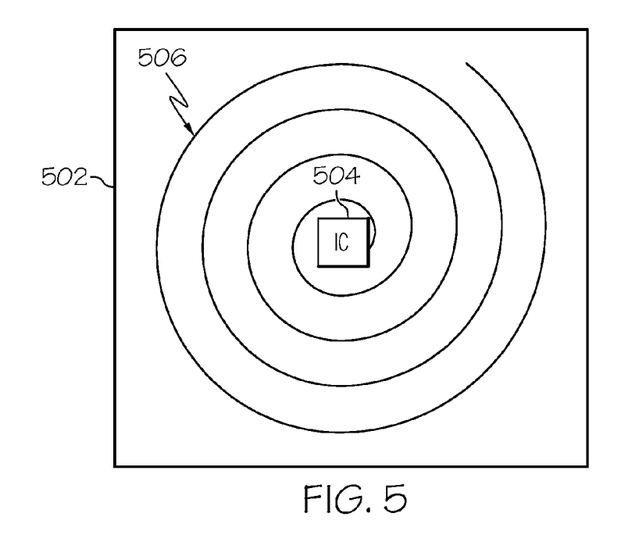
FIG. 5 depicts an exemplary RFID tag that may be used by the present invention.
Figure 6:
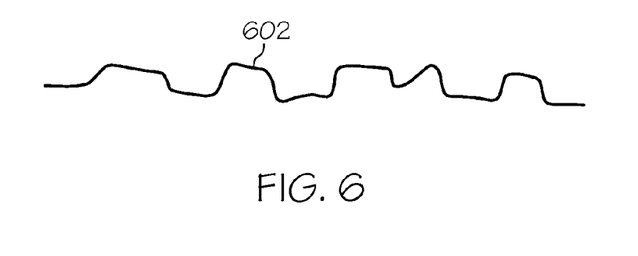
FIG. 6 illustrates an exemplary chipless RFID tag that may be used by the present invention.

With reference now to FIGS. 5-6, exemplary RFID tags are depicted. More specifically, FIG. 5 depicts an exemplary chip-enabled RFID tag 502, which is a passive RFID tag that has an on-board IC chip 504 and a coupled antenna 506. The IC chip 504 stores and processes information, including information that describes the location at which that chip-enabled RFID tag 502 is affixed to a particular pipe.

The IC chip 504 may contain a low-power source (e.g., a capacitor, not shown, that is charged by an interrogation signal received by the coupled antenna 506). Upon the capacitor being charged, the RFID tag 502 then generates a radio signal, which includes the sensor location information stored in the IC chip 504, to be broadcast by the coupled antenna 506.

FIG. 6 illustrates an exemplary chipless RFID tag 602. As the name implies, chipless RFID tag 602 does not have an IC chip, but is only an antenna that is shaped to reflect back a portion of an interrogation signal. That is, the chipless RFID tag 602 (also known as a Radio Frequency (RF) fiber) is physically shaped to reflect back select portions of a radio interrogation signal from an RF transmission source. Chipless RFID tag 602 typically has a much shorter range than that of chip-enabled RFID tag 502. Furthermore, the amount of information that chipless RFID tag 602 can return is much smaller than that of chip-enabled RFID tag 502, which is able to store relatively large amounts of data in the on-board IC chip 504.

Figure 7:
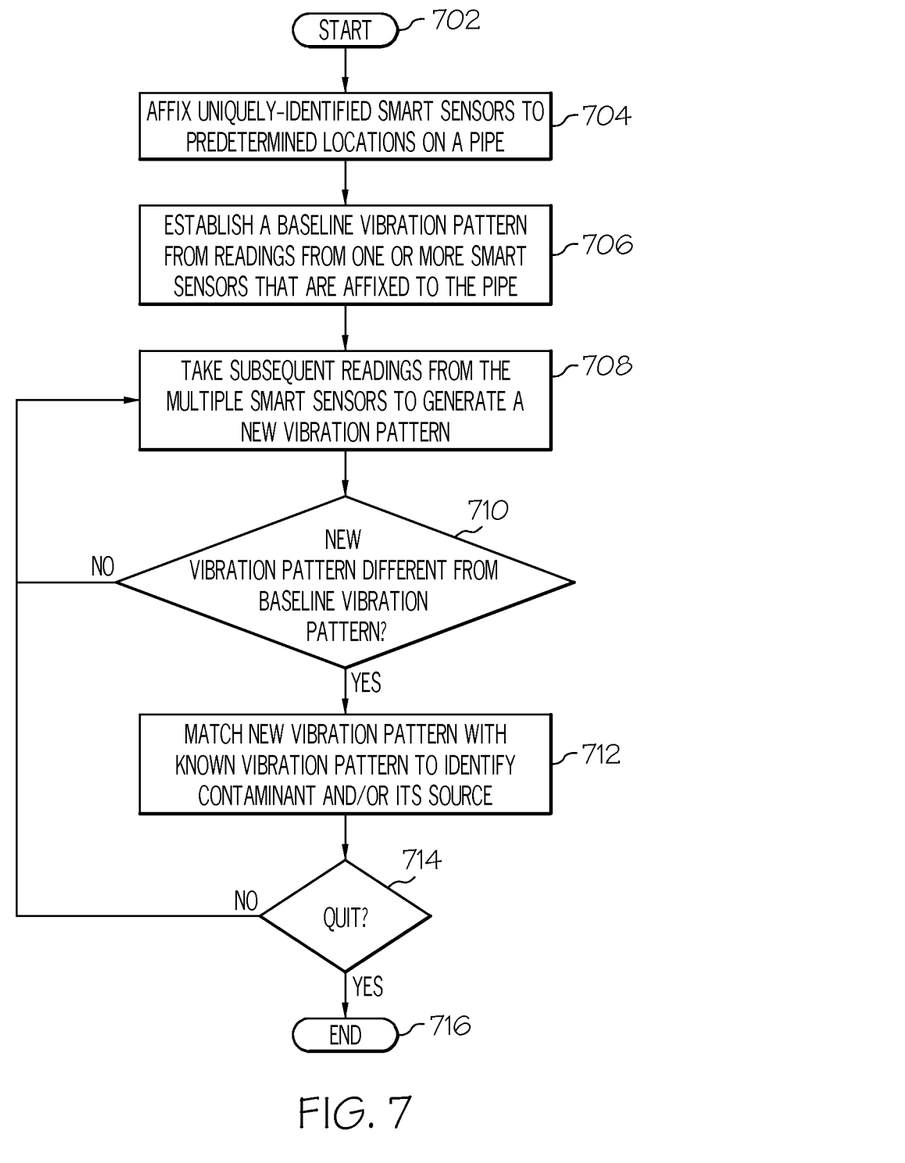
FIG. 7 is a high level flow chart of one or more steps performed by a processor to detect a contaminant in a pipe.

With reference now to FIG. 7, a high level flow chart of one or more steps performed by a processor to detect a contaminant in a fluid-transporting pipe is presented. After initiator block 702, uniquely-identified smart sensors are affixed to predetermined locations on a pipe (block 704). In one embodiment, this pipe is designed to transport only liquids, while in another embodiment it is designed to transport any fluid, whether liquid, gaseous, or slurry, that has a consistency capable of being transported through a pipe. The pipe may be an oil or gas pipeline; a down hole oil/gas drilling/production string or casing; piping in a refinery; water and other fluid piping within a commercial or residential building, etc.

The smart sensors, such as depicted above in FIG. 4, comprise a sensor that is able to detect and transduce vibrations on the exterior surface of the pipe to which the smart sensor is affixed. These vibrations, which are processed to generate vibration patterns (e.g., graphs/records), are the result of the movement of fluids and other material within the interior of the pipe, and/or events (e.g., impact blows, scraping, rubbing, etc.) that are imposed to the exterior of the pipe.

Figure 8:
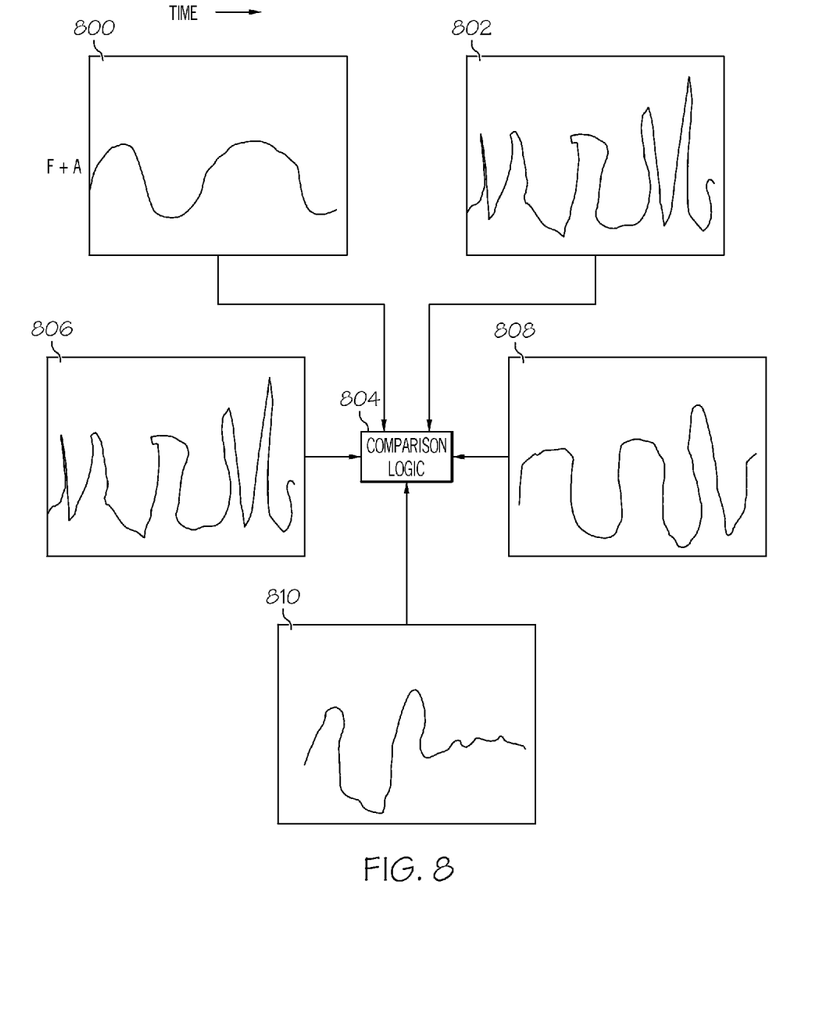
FIG. 8 depicts an exemplary frequency (F) plus amplitude (A) vibration patterns, from a uniquely-identified smart sensor mounted on a pipe, which is then compared to a known vibration pattern in order to identify a cause and/or source of a contaminant to a fluid flowing within the pipe.

As described in block 706, a baseline vibration pattern of vibrations on the exterior surface of the pipe is established from readings generated by one of the smart sensors that are affixed to the pipe. This baseline vibration pattern is caused by a flow of a known liquid as the known liquid travels through the pipe in an unadulterated form, as illustrated above in FIG. 2. As shown in FIG. 8, an exemplary baseline vibration pattern 800, which is generated from readings taken by a smart sensor affixed to a pipe's exterior surface, is depicted. The smart sensor detects and transduces mechanical vibration of the pipe's exterior surface to generate a frequency (F) and amplitude (A) vibration pattern that is baseline vibration pattern 800. As described in block 708 of FIG. 7, subsequent readings are then taken from the smart sensor to generate a new vibration pattern, such as the new vibration pattern 802 depicted in FIG. 8. As described in query block 710 of FIG. 7, a comparison logic (e.g., comparison logic 804 shown in FIG. 8, which may be part of computer 102 and/or CDL 148 shown in FIG. 1, or as part of processing logic 410 shown in FIG. 4) then determines if the new vibration pattern differs from the baseline vibration pattern beyond some predefined range. As depicted in FIG. 8, the baseline vibration pattern 800 clearly differs from the new vibration pattern 802. Due to this difference, the comparison logic 804 then compares the new vibration pattern 802 to stored known vibration patterns 806, 808, and 810. As shown in the example in FIG. 8, the new vibration pattern 802 matches the known vibration pattern 806. The known vibration pattern 806 was created when a specific contaminant was introduced into the fluid that was passing through the pipe in the past, either in the same pipe or a substantially similar pipe (i.e., same material of the pipe, same environment, etc.). That is, known vibration pattern 806 was generated when a substantially similar pipe was transporting a same fluid at a same rate as is currently being transported through the pipe to which the smart sensor is affixed, plus a known contaminant. This historical data may be from measurements taken from physical pipes, including those taken and updated in a neural network, or they may be the result of software simulations of such piping/events/environments. Since the new vibration pattern 802 matches the known vibration pattern 806, a conclusion is reached that the same specific contaminant is once again flowing through the pipe, and thus that specific contaminant is identified as the current contaminant that is now flowing through the pipe (block 712). If a decision is made to quit taking sensor readings on the exterior of the pipe (query block 714), then the process ends (terminator block 716).

The comparison of the new vibration patterns to known vibration patterns for the pipe allow for a fine-grained analysis of the contaminant's identity/classification, as well as the contaminant's source, effects of the contaminant on the pipe, etc.

For example, assume that the specific contaminant in the fluid currently passing through the pipe is a gas contaminant. By storing what the gas-contaminant-to-known-fluid ratio was when the known vibration pattern (e.g., known vibration pattern 806 shown in FIG. 8) was previously created, then when this same vibration pattern occurs again, this same gas-contaminant-to-known-fluid ratio can also be inferred.

This gas-contaminant-to-known-fluid ratio is further used to determine a rate of gas contaminant introduction into the pipe. That is, by knowing the flow rate of the fluid within the pipe, as well as the gas-contaminant-to-known-fluid ratio, then the source of the gas contaminant can also be derived. For example, consider pipe 902 shown in FIG. 9, through which contaminated fluid 904 is passing, and which has a smart sensor 906 affixed to an exterior surface of the pipe 902. There are three possible sources of the gas contaminant: a pinhole leak 908, which is upstream from the smart sensor 906, and which may be allowing a very small amount of air to enter pipe 902; a small pipe 910, which is also upstream from the smart sensor 906, and which may have a faulty valve 912 that is allowing a larger amount of gas from the small pipe 910 to enter pipe 902; and a large pipe 914, which is also upstream from the smart sensor 906, and which may have a faulty valve 916 that is allowing even more gas (than small pipe 910) to enter pipe 902. Thus, by knowing the flow rate of the fluid within the pipe, as well as the gas-contaminant-to-known-fluid ratio, the processor is able to identify the source of the gas contaminant (pinhole leak 912, small pipe 910, or large pipe 914) based on the rate of gas contaminant introduction into the pipe that resulted in the gas-contaminant-to-known-fluid ratio.

Note that the smart sensor detects any vibration on an exterior surface of the pipe. In one embodiment, this external vibration is caused, not only by activity within the pipe, such as turbulence, but also by some event that occurs externally to the pipe. For example a forklift may strike against the pipe, the pipe may shift out of its normal track and hit a structural member, the pipe may shift out of its normal track and land against a rotating device such as a pump shaft, etc. By being able to access a library of known vibration patterns that were generated during such events, a processor is thus able to associate the newly detected external vibration to a specific type of external impact against the exterior of the pipe. Real and/or simulated historical records identify a correlation between that specific type of external impact and a particular vibration pattern, thus confirming the source of the gas contaminant. That is, a known (recorded) vibration pattern reflects the existence of a particular type of impact event occurring against the exterior of the pipe. When this impact event occurred in the past, a specific contaminant was introduced into the pipe, either at the location of the impact (e.g., by knocking a hole somewhere in the pipe) or at another location (e.g., hitting the pipe 902 shown in FIG. 9 may cause one of the valves 912 or 916 to inadvertently open or at least start leaking) By knowing this history and comparing new and known vibration patterns, then the effect of the external impact event is determined based on historical experience. Note again that the flow rate and gas-contaminant-to-known-fluid ratio are unique to each vibration pattern, such that a particular vibration pattern is indicative of a specific flow rate and gas-contaminant-to-known-fluid ratio for a particular fluid flowing through a particular type (size, makeup composition (metal, plastic, etc.), etc.) of pipe.

In another embodiment, assume that the specific contaminant to the fluid passing through the pipe is a liquid contaminant. By storing what the liquid-contaminant-to-known-fluid ratio was when the known vibration pattern (e.g., known vibration pattern 806 shown in FIG. 8) was previously created, this same liquid-contaminant-to-known-fluid ratio can also be inferred when this same vibration pattern occurs once again. This liquid-contaminant-to-known-fluid ratio is then used to determine a rate of liquid contaminant introduction into the pipe. That is, by knowing the flow rate of the fluid within the pipe, as well as the liquid-contaminant-to-known-fluid ratio, then the source of the liquid contaminant can also be derived. For example, consider pipe 902 shown in FIG. 9, through which contaminated fluid 904 is passing, and which has a smart sensor 906 affixed to an exterior surface of the pipe 902. There are two possible sources of the liquid contaminant: small pipe 910, which is also upstream from the smart sensor 906, and which may have a faulty valve 912 that is allowing a small amount of liquid from the small pipe 910 to enter pipe 902; and large pipe 914, which is also upstream from the smart sensor 906, and which may have a faulty valve 916 that is allowing even more liquid (a larger amount than what small pipe 910 could introduce) to enter pipe 902. Thus, by knowing the flow rate of the fluid within the pipe, as well as the liquid-contaminant-to-known-fluid ratio, the processor is able to identify the source of the liquid contaminant (small pipe 910 or large pipe 914) based on the rate of liquid contaminant introduction into the pipe that resulted in the liquid-contaminant-to-known-fluid ratio. As with the gas contaminant described above, the flow rate and liquid-contaminant-to-known-fluid ratio are unique to each vibration pattern.

Figure 9:
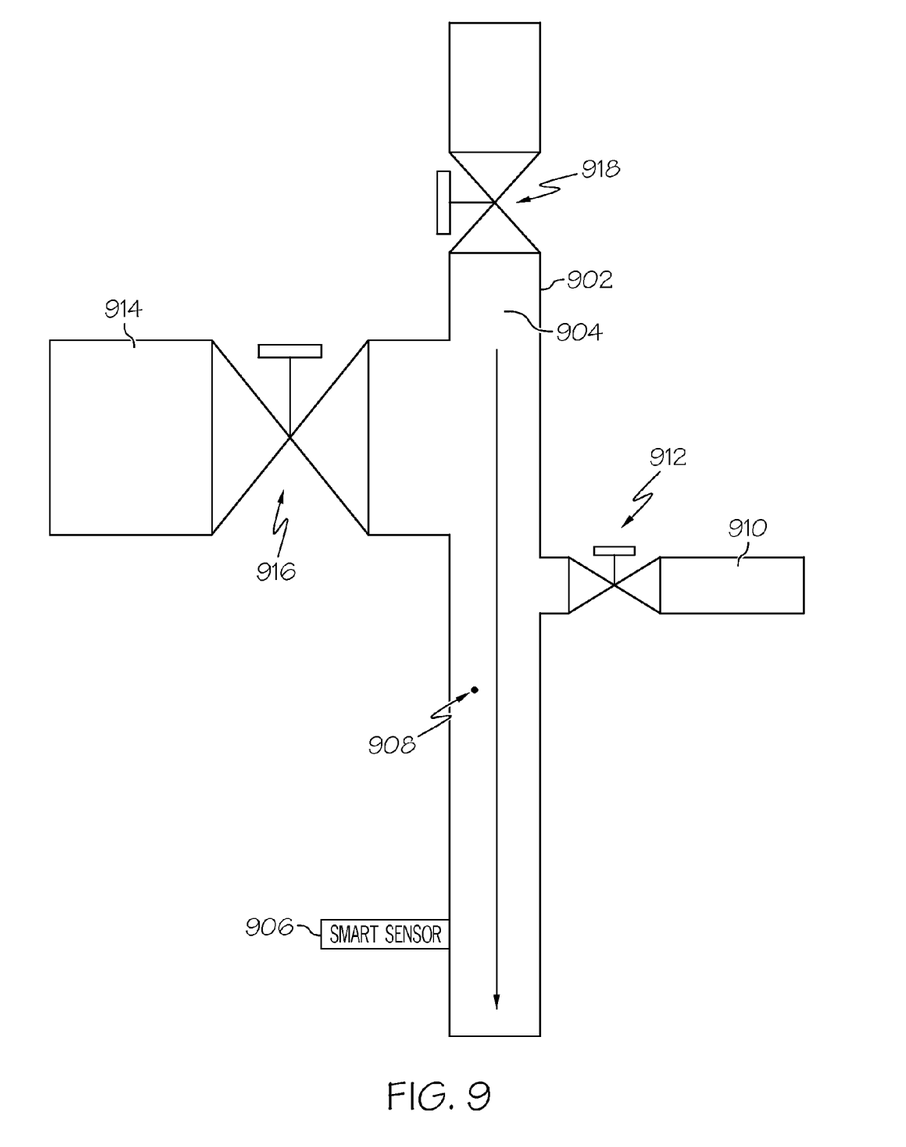
FIG. 9 illustrates additional detail of the pipe shown in FIGS. 2-3.

As with the gas contaminant described above, in one embodiment, the smart sensor detects an external vibration on an exterior of the pipe. This external vibration is caused, not by activity within the pipe, such as turbulence, but rather by some event that occurs external to the pipe. For example a forklift may strike against the pipe, the pipe may shift out of its normal track and hit a structural member, the pipe may shift out of its normal track and land against a rotating device such as a pump shaft, etc. By being able to access a library of known vibration patterns that were generated from such events, a processor is thus able to associate the newly detected external vibration to a specific type of external impact against the exterior of the pipe. As real and/or simulated historical records identify a correlation between that specific type of external impact and a particular vibration pattern, thus confirming the source of the liquid contaminant. That is, if a known (recorded) vibration pattern shows that when a particular type of impact event occurs against the exterior of the pipe, then this impact event results in a liquid contaminant being introduced into the pipe, either at the location of the impact (e.g., by directly striking one of the valves 912/916 to be knocked ajar, if not opened fully) or at another location (e.g., hitting the pipe 902 at a location away from large pipe 914 or small pipe 910 may cause one of the valves 912 or 916 to inadvertently open).

In one embodiment, the specific contaminant is a solid contaminant. In a process similar to that described above for gas and liquid contaminants, a solid-contaminant-to-known-fluid ratio is determined based on the new vibration pattern, thus enabling the determination of a rate of solid contaminant introduction into the pipe based on the determined solid-contaminant-to-known-fluid ratio and flow rate through the pipe, as well as the source of the solid contaminant based on the rate of solid contaminant introduction into the pipe.

In one embodiment, the solid contaminant is from delamination (i.e., scaling and sloughing off) of the interior wall of the pipe 902. The amount of delamination is determined by measuring how long the new vibration pattern, which was caused by the delamination, is being observed/generated by the smart sensor and/or computer. For example, if a new vibration pattern continues to be observed over the course of a month, then, based on the known amount of solid contaminant that is passing through the pipe (based on the solid-contaminant-to-known-fluid ratio and known flow-rate of material through the pipe), then the total amount of delamination is calculated. This calculation leads to a determination of how much the pipe interior has eroded, in order to determine if the pipe has become so thin as to pose an operational/safety hazard.

In another embodiment, the solid contaminant is from a degraded valve that is upstream from the smart sensor. For example, assume that the valve 918 shown in FIG. 9 is corroding, leading to metal particles being introduced into the interior of otherwise normally operating pipe 902. As with the delamination example described above, measuring the length of time of the new vibration pattern, which is caused by the introduction of metal particles from valve 918 into the flow within pipe 902, enables a processor to calculate the total amount of metal particles that have been lost from the valve 918. This calculation is then used to predict when the valve 918 will fail if not repaired/replaced. That is, the remaining lifetime of valve 918 is determined by measuring an amount of time that the new vibration pattern (which resulted from the introduction of the metal particles from the valve 918 into the interior flow of pipe 902) is being generated by the smart sensor/processor.

In one embodiment, the smart sensor 906 shown in FIG. 9 has an RFID tag (see element 412 in FIG. 4), thus making smart sensor 906 a uniquely-identified radio frequency identifier (RFID) device. That is, in this embodiment, the smart sensor 906 is able to not only identify itself, but can also identify its exact location by mapping a location of the smart sensor 906 based on the ID of smart sensor (e.g., through an interrogation of the RFID device/tag in the smart sensor 906). By using this location information, a processor is able to modify the new vibration pattern to create a location-dependent new vibration pattern according to the location of the smart sensor. For example, if the smart sensor 906 shown in FIG. 9 were relocated closer to pinhole leak 908, then smart sensor 906 would detect/measure/quantify/display more fluid turbulence within pipe 902 than if the smart sensor 906 remained in the original location shown in FIG. 9. This difference would be due to additional eddy turbulence that appears at the source of the gas entering the pipe 902 through the pinhole leak 908. As the gas contaminant moves through the interior of pipe 902, this turbulence abates. This level of abatement is thus used to identify the location of the source of the gas contaminant. Thus, an identified location of the source of the gas contaminant is adjusted (or established) based on the location-dependent new vibration pattern.

In one embodiment, the new vibration pattern is used to determine the specific gravity of the specific contaminant. That is, each vibration pattern is unique not only to the type (gas, liquid, solid) of contaminant that is introduced into the flow, but also is unique to the specific gravity of the introduced contaminant. For example, assume that in one scenario a first liquid contaminant has a high specific gravity (particularly when compared to the unadulterated fluid that is passing through the pipe), while a second liquid contaminant has a relatively lower (when compared to the first liquid contaminant) specific gravity. These different specific gravities cause different turbulence patterns, which result in new vibration patterns that are matched to turbulence/vibration patterns of known turbulence/vibration patterns that were generated when a particular liquid contaminant, having the same specific gravity as the new contaminant, was introduced into the pipe.

In one embodiment, a rate of change to a defect in the pipe is determined based on a sequence of changes to new vibration patterns. For example, assume that the source of a specific contaminant is a defect that is upstream from a position on the pipe to which the smart sensor is affixed. By utilizing the process described above, a processor can identifying the defect (what it is and/or where it is located) based on the new vibration pattern. A series of new vibration patterns are then generated by the smart sensor and/or processor. By identifying how these patterns change (i.e., by identifying a sequence of changes to new vibration patterns that are generated by the smart sensor), the rate of change in the defect (i.e., how rapidly the defective valve, pinhole, etc. is "getting worse") is identified based on the sequence of changes to the new vibration patterns.

In one embodiment, the source of the contaminant is determined based on subsequent new vibration patterns fluctuating in a cyclic manner. For example, assume that valve 918 in FIG. 9 is erroneously opening and closing every 60 seconds due to a faulty actuator (not shown) that controls the valve 918. This opening and closing results in a distinctive set of new vibration patterns being generated by the smart sensor. Thus, a processor is able to detect these cyclic changes in the new vibration patterns, in order to match these cyclic changes in the new vibration patterns to known vibration patterns. This matching identifies the malfunctioning upstream mechanical device (e.g., cyclically opening/closing valve 918) in order to identify the source of the specific contaminant.

Note that in one embodiment, the baseline vibration pattern may be taken while a single anomalous event occurs. That is, assume that while the baseline vibration pattern described above is being generated, a worker inadvertently taps the side of the pipe with his tool belt, thus potentially disrupting the baseline vibration pattern. Through heuristic neural network derived information, a processor will "recognize" this impact as an anomalous event, and will filter it out of the baseline vibration pattern. Thus, if and when the pipe is subjected to a known anomalous event, the processor filters out vibrations that are caused by the known anomalous event in order to prevent the known anomalous event from affecting the baseline vibration pattern.

In one embodiment, the pipe may be subjected to an anomalous event (e.g., being struck by a forklift) after the new vibration pattern was generated. This event, due to its severity, may cause a catastrophic failure to the pipe. However, this catastrophic failure may not actually manifest itself for hours, days, or even weeks after the anomalous event (e.g., being struck) occurred. In this embodiment, therefore, a subsequent new vibration pattern that includes new vibrations caused by the anomalous event is generated. Using a library of known and/or simulated vibration patterns, a processor is thus able to identify the anomalous event based on the new vibrations. By knowing what caused the new vibrations and their historic consequences (i.e., past results that have occurred due to this type of anomalous event) in the past, the processor then predicts a catastrophic future event to the pipe based on the identified anomalous event.

Note further that in various embodiments, reference is made to comparing the baseline vibration pattern to a new vibration pattern, which is then compared to a stored known vibration pattern. In one embodiment, this comparison is performed by performing a Fast Fourier Transform (FFT) analysis on the various vibration patterns, in order to determine a set of underlying frequency components. These frequency components can then be digitized for storage and rapid future comparison operations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A method of detecting an amount of delamination of an interior wall of a pipe that is transporting a known fluid, the computer-implemented method comprising:
   establishing, by one or more processors, a baseline vibration pattern from readings generated by a smart sensor that is affixed to the pipe, wherein the baseline vibration pattern is caused by a flow of the known fluid as the known fluid travels through the pipe in an unadulterated form;
   taking, by one or more processors, subsequent readings from the smart sensor to generate a new vibration pattern;
   in response to the new vibration pattern being different, beyond a predefined range, from the baseline vibration pattern, matching, by one or more processors, the new vibration pattern with a known vibration pattern in order to identify a specific contaminant of the known fluid, wherein the specific contaminant is a solid contaminant, wherein the known vibration pattern is known to occur when the specific contaminant is flowing through the pipe with the known fluid;
   determining, by one or more processors, a solid-contaminant-to-known-fluid ratio based on the new vibration pattern;
   determining, by one or more processors, a rate of solid contaminant introduction into the pipe based on the determined solid-contaminant-to-known-fluid ratio;
   determining, by one or more processors and based on the rate of solid contaminant introduction into the pipe, that the solid contaminant is caused by a delamination of an interior wall of the pipe;
   determining, by one or more processors, an amount of delamination of the interior wall of the pipe by measuring an amount of time that the new vibration pattern is being generated; and
   determining, by one or more processors, a specific gravity of the specific contaminant by matching the new vibration pattern with the known vibration pattern.

2. The method of claim 1, wherein the smart sensor comprises a uniquely-identified radio frequency identifier (RFID) device, and wherein the computer-implemented method further comprises:
   mapping, by one or more processors, a location of the smart sensor by interrogating an RFID device in the smart sensor; and
   modifying, by one or more processors, the new vibration pattern to create a location-dependent new vibration pattern according to the location of the smart sensor.

3. The method of claim 1, further comprising:
   detecting, by one or more processors, a cyclic change in vibration patterns generated by the subsequent readings from the smart sensor; and
   matching, by one or more processors, the cyclic change in vibration pattern changes to a malfunctioning upstream mechanical device in order to identify a secondary source, beyond said delamination of the interior wall of the pipe, of the specific contaminant.

4. The method of claim 1, wherein the pipe is subjected to a known anomalous event, and wherein the method further comprises:
   filtering out, by one or more processors, vibrations that are caused by the known anomalous event in order to prevent the known anomalous event from affecting the baseline vibration pattern.

5. The method of claim 1, wherein the pipe is subjected to an anomalous event after the new vibration pattern was generated, and wherein the method further comprises:
   generating, by one or more processors, a subsequent new vibration pattern that includes new vibrations caused by the anomalous event;
   identifying, by one or more processors, the anomalous event based on the new vibrations; and
   predicting, by one or more processors, a catastrophic future event to the pipe based on the identified anomalous event.

6. A computer program product for detecting an amount of delamination of an interior wall of a pipe that is transporting a known fluid, the computer program product comprising a non-transitory computer readable medium containing computer instructions stored therein for causing a computer processor to perform:
   establishing a baseline vibration pattern from readings generated by a smart sensor that is affixed to the pipe, wherein the baseline vibration pattern is caused by a flow of the known fluid as the known fluid travels through the pipe in an unadulterated form;
   taking subsequent readings from the smart sensor to generate a new vibration pattern;
   in response to the new vibration pattern being different, beyond a predefined range, from the baseline vibration pattern, matching the new vibration pattern with a known vibration pattern in order to identify a specific contaminant of the known fluid, wherein the specific contaminant is a solid contaminant, wherein the known vibration pattern is known to occur when the specific contaminant is flowing through the pipe with the known fluid;

determining a solid-contaminant-to-known-fluid ratio based on the new vibration pattern;

determining a rate of solid contaminant introduction into the pipe based on the determined solid-contaminant-to-known-fluid ratio;

determining, based on the rate of solid contaminant introduction into the pipe, that the solid contaminant is caused by a delamination of an interior wall of the pipe;

determining an amount of delamination of the interior wall of the pipe by measuring an amount of time that the new vibration pattern is being generated; and determining a specific gravity of the specific contaminant by matching the new vibration pattern with the known vibration pattern.

7. The computer program product of claim 6, wherein the smart sensor comprises a uniquely-identified radio frequency identifier (RFID) device, and wherein the computer instructions further causing a computer processor to perform:

mapping a location of the smart sensor by interrogating an RFID device in the smart sensor; and modifying the new vibration pattern to create a location-dependent new vibration pattern according to the location of the smart sensor.

8. The computer program product of claim 6, wherein the computer instructions further causing a computer processor to perform:

detecting a cyclic change in vibration patterns generated by the subsequent readings from the smart sensor; and matching the cyclic change in vibration pattern changes to a malfunctioning upstream mechanical device in order to identify a secondary source, beyond said delamination of the interior wall of the pipe, of the specific contaminant.

9. The computer program product of claim 6, wherein the pipe is subjected to a known anomalous event, and wherein the computer instructions further causing a computer processor to perform:

filtering out vibrations that are caused by the known anomalous event in order to prevent the known anomalous event from affecting the baseline vibration pattern.

10. The computer program product of claim 6, wherein the pipe is subjected to an anomalous event after the new vibration pattern was generated, and wherein the computer instructions further causing a computer processor to perform:

generating a subsequent new vibration pattern that includes new vibrations caused by the anomalous event;

identifying the anomalous event based on the new vibrations; and predicting a catastrophic future event to the pipe based on the identified anomalous event.

11. A system comprising:

a processor, a computer readable memory, and a non-transitory computer readable storage medium;

first program instructions to establish a baseline vibration pattern from readings generated by a smart sensor that is affixed to the pipe, wherein the baseline vibration pattern is caused by a flow of the known fluid as the known fluid travels through the pipe in an unadulterated form;

second program instructions to take subsequent readings from the smart sensor to generate a new vibration pattern;

third program instructions to, in response to the new vibration pattern being different, beyond a predefined range, from the baseline vibration pattern, match the new vibration pattern with a known vibration pattern in order to identify a specific contaminant of the known fluid, wherein the specific contaminant is a solid contaminant, wherein the known vibration pattern is known to occur when the specific contaminant is flowing through the pipe with the known fluid;

fourth program instructions to determine a solid-contaminant-to-known-fluid ratio based on the new vibration pattern;

fifth program instructions to determine a rate of solid contaminant introduction into the pipe based on the determined solid-contaminant-to-known-fluid ratio;

sixth program instructions to determine, based on the rate of solid contaminant introduction into the pipe, that the solid contaminant is caused by a degradation of a valve that is upstream of the smart sensor;

seventh program instructions to determine a remaining lifetime of the valve by measuring an amount of time that the new vibration pattern is being generated; and eighth program instructions to determine a specific gravity of the specific contaminant by matching the new vibration pattern with the known vibration pattern; and wherein the first, second, third, fourth, fifth, sixth, seventh, and eighth program instructions are stored on the non-transitory computer readable storage medium, and wherein the program instructions are executed by the processor via the computer readable memory.

12. The system of claim 11, wherein the smart sensor comprises a uniquely-identified radio frequency identifier (RFID) device, and wherein the system further comprises:

ninth program instructions to map a location of the smart sensor by interrogating an RFID device in the smart sensor; and tenth program instructions to modify the new vibration pattern to create a location-dependent new vibration pattern according to the location of the smart sensor; and wherein the ninth and tenth program instructions are stored on the non-transitory computer readable storage medium, and wherein the program instructions are executed by the processor via the computer readable memory.

13. The system of claim 11, wherein the system further comprises:

ninth program instructions to detect a cyclic change in vibration patterns generated by the subsequent readings from the smart sensor; and tenth program instructions to match the cyclic change in vibration pattern changes to a malfunctioning upstream mechanical device in order to identify a secondary source, beyond said delamination of the interior wall of the pipe, of the specific contaminant; and wherein the ninth and tenth program instructions are stored on the non-transitory computer readable storage medium, and wherein the program instructions are executed by the processor via the computer readable memory.

14. The system of claim 11, wherein the pipe is subjected to a known anomalous event, and wherein the system further comprises:

ninth program instructions to filter out vibrations that are caused by the known anomalous event in order to prevent the known anomalous event from affecting the baseline vibration pattern; and wherein the ninth program instructions are stored on the non-transitory computer readable storage medium, and wherein the program instructions are executed by the processor via the computer readable memory.

15. The system of claim 11, wherein the pipe is subjected to an anomalous event after the new vibration pattern was generated, and wherein the system further comprises:
- ninth program instructions to generate a subsequent new vibration pattern that includes new vibrations caused by the anomalous event;
- tenth program instructions to identify the anomalous event based on the new vibrations; and
- eleventh program instructions to predict a catastrophic future event to the pipe based on the identified anomalous event; and wherein the ninth, tenth, and eleventh program instructions are stored on the non-transitory computer readable storage medium, and wherein the program instructions are executed by the processor via the computer readable memory.

* * * * *